(12) United States Patent
Huang et al.

(10) Patent No.: US 10,420,787 B2
(45) Date of Patent: Sep. 24, 2019

(54) CRYSTAL-WATER-FREE CALCIUM DIBUTYRYLADENOSINE CYCLOPHOSPHATE CRYSTAL FORM AND PREPARATION METHOD AND APPLICATION THEREOF

(71) Applicants: SPH NO.1 BIOCHEMICAL & PHARMACEUTICAL CO., LTD., Shanghai (CN); SHANGHAI ZIYUAN PHARMACEUTICAL CO., LTD., Shanghai (CN)

(72) Inventors: Zhenhui Huang, Shanghai (CN); Liuqing Yang, Shanghai (CN); Jianli Huo, Shanghai (CN); Xinlei Zhu, Shanghai (CN); Jinguo Ding, Shanghai (CN); Zhigang Zhang, Shanghai (CN)

(73) Assignees: SPH NO.1 BIOCHEMICAL & PHARMACEUTICAL CO., LTD., Shanghai (CN); SHANGHAI ZIYUAN PHARMACEUTICAL CO., LTD., Shanghai (CN)

( * ) Notice: Subject to any disclaimer, the term of this patent is extended or adjusted under 35 U.S.C. 154(b) by 75 days.

(21) Appl. No.: 15/525,049

(22) PCT Filed: Mar. 5, 2015

(86) PCT No.: PCT/CN2015/073668
§ 371 (c)(1),
(2) Date: Dec. 18, 2017

(87) PCT Pub. No.: WO2016/101412
PCT Pub. Date: Jun. 30, 2016

(65) Prior Publication Data
US 2018/0050057 A1    Feb. 22, 2018

(30) Foreign Application Priority Data
Dec. 24, 2014  (CN) .......................... 2014 1 0840112

(51) Int. Cl.
*A61K 31/7076* (2006.01)
*C07H 1/06* (2006.01)
*C07H 19/213* (2006.01)
*C07F 9/6574* (2006.01)
*G01N 21/35* (2014.01)
*G01N 23/20* (2018.01)
*G01N 25/48* (2006.01)

(52) U.S. Cl.
CPC .......... *A61K 31/7076* (2013.01); *C07H 1/06* (2013.01); *C07H 19/213* (2013.01); *C07B 2200/13* (2013.01); *C07F 9/65744* (2013.01); *G01N 21/35* (2013.01); *G01N 23/20075* (2013.01); *G01N 25/4866* (2013.01)

(58) Field of Classification Search
CPC ..... A61K 31/7076; C07H 1/06; C07H 19/213
See application file for complete search history.

(56) References Cited

FOREIGN PATENT DOCUMENTS

| CN | 1554358 A | 12/2004 |
|---|---|---|
| CN | 1931180 A | 3/2007 |
| CN | 101020707 A | 8/2007 |
| CN | 101172112 A | 5/2008 |
| CN | 103242403 A | 8/2013 |
| CN | 104262436 A | 1/2015 |
| JP | 1976-113896 A | 10/1976 |

OTHER PUBLICATIONS

Orglab; http://www.umsl.edu/~orglab/pdffiles/practice.pdf (Oct. 5, 1999).*

* cited by examiner

*Primary Examiner* — Pancham Bakshi
(74) *Attorney, Agent, or Firm* — Wayne & Ken, LLC; Tony Hom

(57) ABSTRACT

Disclosed are a crystallization water-free calcium dibutyryladenosine cyclophosphate crystal form, and a preparation method and a use thereof. In an X-ray powder diffraction pattern using Cu-Kα as a source of radiation, the crystallization water-free calcium dibutyryladenosine cyclophosphate crystal form has characteristic peaks at positions where diffraction angles 2θ are equal to 12.3°±0.2°, 17.6°±0.2°, 21.4°±0.2°, 24.7°±0.2°, 25.3°±0.2° and 27.8°±0.2°. The crystallization water-free calcium dibutyryladenosine cyclophosphate crystal form of the present invention has a high purity, and good stability; the preparation method is simple and convenient, has good reproducibility, and is easy to industrially popularize and apply.

4 Claims, 4 Drawing Sheets

CRYSTAL-WATER-FREE CALCIUM DIBUTYRYLADENOSINE CYCLOPHOSPHATE CRYSTAL FORM AND PREPARATION METHOD AND APPLICATION THEREOF

TECHNICAL FIELD

The present invention relates to the field of medicines, and more specifically, to a crystal-water-free calcium dibutyryladenosine cyclophosphate crystal form and a preparation method and an application thereof.

BACKGROUND OF THE INVENTION

Calcium dibutyryladenosine cyclophosphate is a product prepared from a calcium salt formed by abutyrylation derivative of Cyclic Adenosine Monophosphate (cAMP). Calcium adenosine diphosphate serves as a protein kinase activator, and can simultaneously activate protein kinase A and protein kinase C (cAMP can only activate protein kinase A). The protein kinase is an allosteric enzyme and is composed of two catalytic subunits and two regulatory subunits, and the catalytic subunits have effects of catalyzing protein (or enzyme) phosphonation. Therefore, the calcium adenosine diphosphatecan catalyze the most basic biochemical metabolism in a human body, that is, oxidative phosphorylation and tricarboxylic acid cycle, so that most of proteins and enzymes produce activities, activate various reactions of the human body and produce lots of ATPs to improve cells and energy metabolism, thereby achieving the effects of promoting nerve regeneration, transforming abnormal cells, dilating blood vessels, relaxing smooth muscle, improving myocardial ischemia, etc.

The calcium dibutyryladenosine cyclophosphate is mainly used for clinical treatment of stenocardia and acute myocardial infarction, also can be used for treating myocarditis, cardiogenic shock, postoperative retinal hemorrhage and psoriasis, and can further serve as an auxiliary anti-cancer drug to be used for clinical treatment of diseases, such as leukemia, etc.

However, amorphous crude drugs or injection preparations of the calcium dibutyryladenosine cyclophosphate easily generate drug degradation during an expiration date so as to produce related substances, so that adverse drug reactions, such as heart failure and death caused by anaphylactic shock, placenta teratogenesis, etc. may be increased. The study has found that the root cause of the adverse reactions is the instability defect of the calcium dibutyryladenosine cyclophosphate.

Different crystal forms of one compound are known as "multi-crystal-form variants" or "polymorphic substances". Although the polymorphic substances have identical chemical structures, obvious differences in aspects of drug stability, bioavailability, etc. will be caused due to differences of the substances in packing arrangement and geometrical arrangement, so that drug quality stability and curative effects of drugs are directly influenced. Therefore, a relatively stable drug crystal form has an important value for improving clinical curative effects of the drugs during the expiration date.

SUMMARY OF THE INVENTION

A technical problem to be solved in the present invention is to overcome a defect in the existing technology that an amorphous substance of calcium dibutyryladenosine cyclophosphate has instable drug quality during an expiration date. The present invention provides a crystal-water-free calcium dibutyryladenosine cyclophosphate crystal form and a preparation method thereof, a pharmaceutical composition of the crystal-water-free calcium dibutyryladenosine cyclophosphate crystal form and a preparation method thereof, as well as an application of the crystal-water-free calcium dibutyryladenosine cyclophosphate crystal form in preparation of medicines for treating cardiovascular and cerebrovascular diseases. The crystal-water-free calcium dibutyryladenosine cyclophosphate crystal form in the present invention has the advantages of high purity, high stability and simplicity and convenience in preparation method, high reproducibility and convenience for industrialized popularization and application.

The present invention solves the technical problem above by virtue of the following technical solutions:

The present invention provides the crystal-water-free calcium dibutyryladenosine cyclophosphate crystal form. The crystal-water-free calcium dibutyryladenosine cyclophosphate crystal form has characteristic peaks at diffraction angles 2θ of 12.3°±0.2°, 17.6°±0.2, 21.4°±0.2°, 24.7°±0.2, 25.3°±0.2° and 27.8°±0.2° in an X-ray powder diffraction pattern by taking Cu-Kα as a radiation source, wherein, preferably, the crystal form has secondary peaks at diffraction angles 2θ of 5.3°±0.2°, 18.0°±0.2°, 33.2°±0.2°, 35.2°±0.2°, 37.4°±0.2°, 39.2°±0.2°, 43.4°±0.2° and 50.8°±0.2° in the X-ray powder diffraction pattern.

Preferably, the characteristic peaks at the diffraction angles 2θ have relative intensities shown in the following tables:

| Diffraction peak No. | 2θ angle (°) | Interplanar spacing (Å) | Relative intensity (%) |
| --- | --- | --- | --- |
| 1 | 5.3 ± 0.2 | 16.684 | 7 |
| 2 | 12.3 ± 0.2 | 7.164 | 100 |
| 3 | 17.6 ± 0.2 | 5.040 | 20 |
| 4 | 18.0 ± 0.2 | 4.914 | 8 |
| 5 | 21.4 ± 0.2 | 4.152 | 56 |
| 6 | 24.7 ± 0.2 | 3.599 | 58 |
| 7 | 25.3 ± 0.2 | 3.518 | 26 |
| 8 | 27.8 ± 0.2 | 3.211 | 54 |
| 9 | 33.2 ± 0.2 | 2.694 | 14 |
| 10 | 35.2 ± 0.2 | 2.544 | 7 |
| 11 | 37.4 ± 0.2 | 2.405 | 13 |
| 12 | 39.2 ± 0.2 | 2.294 | 6 |
| 13 | 43.4 ± 0.2 | 2.085 | 11 |
| 14 | 50.8 ± 0.2 | 1.794 | 9 |

In the present invention, the X-ray powder diffraction pattern of the crystal-water-free calcium dibutyryladenosine cyclophosphate crystal form is shown in FIG. 1.

In the present invention, the crystal-water-free calcium dibutyryladenosine cyclophosphate crystal form has infrared absorption characteristic peaks at wave numbers of 2974, 1751, 1704, 1619, 1465, 1256, 1105 and 1022 cm$^{-1}$ in an infrared spectrogram; preferably, the infrared spectrogram of the crystal-water-free calcium dibutyryladenosine cyclophosphate crystal form is shown in FIG. 2.

In the present invention, the crystal-water-free calcium dibutyryladenosine cyclophosphate crystal form has a maximum absorption peak at a temperature of 120° C.-170° C. in a differential scanning calorimetry (DSC) map, preferably the crystal form has the maximum absorption peak at a temperature of 149.4° C.; and more preferably the DSC map of the crystal-water-free calcium dibutyryladenosine cyclophosphate crystal form is shown in FIG. 3.

The present invention further provides a method for preparing the crystal-water-free calcium dibutyryladenosine cyclophosphate crystal form. The method includes the following steps: mixing anhydrouscalcium dibutyryladenosine cyclophosphate solids with solvents, heating and dissolving, performing activated carbon decoloration, filtering insoluble substances, adding anti-solvents into filtrate, cooling, stirring and crystallizing, thereby obtaining the product, wherein, the solvents preferably are one or more of methanol, ethanol, isopropanol, ethylene glycol, acetonitrile, tetrahydrofuran, dioxane, ethyl acetate, dichloromethane, acetone and chloroform;

the anti-solvents preferably are one or more of normal hexane, n-pentane, ethyl ether, isopropyl ether, methyl tertiary butyl ether and methylbenzene;

a preferable volume mass ratio of the solvents to the anhydrouscalcium dibutyryladenosine cyclophosphate solids is 2-10 mL/g;

the heating and dissolving temperature is preferably 25° C.-60° C.; and a preferable mass ratio of activated carbon to anhydrouscalcium dibutyryladenosine cyclophosphate solids is (0.01-0.1):(1).

In the present invention, the anhydrouscalcium dibutyryladenosine cyclophosphate solids are preferably amorphous substances of anhydrouscalcium dibutyryladenosine cyclophosphate;

wherein the cooling, stirring and crystallizing temperature is preferably −25° C.~25° C.;

an addition manner of the anti-solvents is preferably dripping, and the dripping rate is preferably 0.3-2.0 mL/min; and the cooling, stirring and crystallizing time is preferably 1-24 h.

The present invention further provides a pharmaceutical composition including the crystal-water-free calcium dibutyryladenosine cyclophosphate crystal form above and a pharmaceutically acceptable carrier.

The present invention further provides a method for preparing the pharmaceutical composition above. The method includes the following steps: mixing the crystal-water-free calcium dibutyryladenosine cyclophosphate crystal form above with the pharmaceutically acceptable carrier, thereby obtaining the product.

The present invention further provides an application of the crystal-water-free calcium dibutyryladenosine cyclophosphate crystal form in preparation of medicines for treating human cardiovascular and cerebrovascular diseases.

In the present invention: a term "XRPD" refers to X-ray powder diffraction;

a term "IR" refers to infrared spectroscopy;

a term "DSC" refers to differential scanning calorimetry;

a term "HPLC" refers to high performance liquid chromatography;

a term "$^1$HNMR" refers to hydrogen nuclear magnetic resonance;

a term "MS" refers to mass-spectrography;

a term "anti-solvent" refers to a solvent which is miscible with solvents and cannot dissolve solutes.

The crystal-water-free calcium dibutyryladenosine cyclophosphate crystal form provided by the present invention is determined by the XRPD, IR and DSC maps.

On the basis of complying with common sense in the field, the optimized conditions above can be optionally combined, thereby obtaining each preferable example of the present invention.

The reagents and raw materials used in the present invention are commercially available.

The present invention has the following positive progresses and effects that:

(1) The crystal-water-free calcium dibutyryladenosine cyclophosphate crystal form in the present invention has the advantages of high purity, high stability and simplicity and convenience in preparation method, high reproducibility and convenience for industrialized popularization and application.

(2) Data acquisition and analysis and experimental research of the crystal-water-free calcium dibutyryladenosine cyclophosphate crystal form in the present invention contribute to developing a drug crystal form which is moisture/light/heat-stable, which is favorable for solving a technical problem existing in this field for a long time that related substances are increased in a storage period of drugs (raw drugs or injection preparations) during the expiration date, and improving the quality and clinical curative effects of calcium dibutyryladenosine cyclophosphate products.

DETAILED DESCRIPTION OF THE INVENTION

Figure 1:
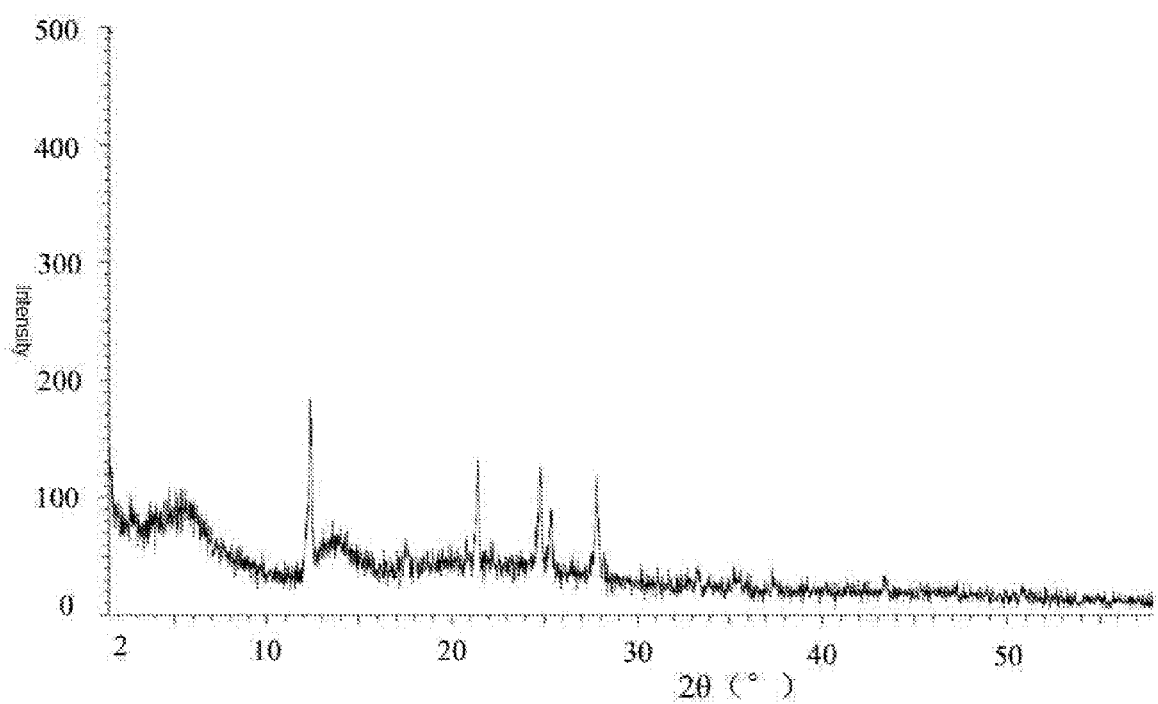
FIG. 1 is an X-ray powder diffraction pattern of a crystal-water-free calcium dibutyryladenosine cyclophosphate crystal form prepared by the present invention.

A crystal-water-free calcium dibutyryladenosine cyclophosphate crystal form provided by the present invention is determined by the XRPD. IR and DSC maps.

(1) X-Ray Powder Diffraction

The X-ray powder diffraction is performed by using a D8 ADVANCE X-ray powder diffractometer from German company BRUKER-AXS, and test conditions include:

a Cu target, a Kα light source (λ=1.54056 Å), working voltage of 40 KV, working current of 40 mA, step length of 0.02, a scanning speed of 0.3 second per step, and a scanning angle of 1.5°-60.0°.

(2) A Hydrogen Nuclear Magnetic Resonance Detection Method

The hydrogen nuclear magnetic resonance detection method is performed by using Avance III 400 MHz from Company Bruker, and a test method includes the steps: adding 5 mg of the calcium dibutyryladenosine cyclophosphate crude drug or crystal form into a nuclear magnetic resonance tube, dissolving by using deuterium oxide, scanning and obtaining the hydrogen nuclear magnetic resonance.

(3) Mass Spectrometry

The mass spectrometry is performed by using ACQUITY™ UPLC&Q-TOF MS Premier from an American company Waters, and a test method is as follows:

the chromatographic column is a Waters Acquity BEH C18 chromatographic column (2.1*100 mm, 1.7 um), a tandem mass spectrometry ionization source refers to an electrospray ionization source (ESI), detection is performed in a positive ion scanning manner, a capillary voltage is 3.0 kV, a temperature of the ionization source is 100° C., a temperature of atomization gas is 350° C., flow of the atomization gas is 600.0 L-hr-1, collision voltages are respectively 4.0 eV (MS) and 15.0-30.0 eV (MS/MS), and a scanning range is m/z 100-1000.

(4) HPLC Detection Method

HPLC detection is performed by using an American Waters 2695 high performance liquid chromatograph, an automatic sampler, a Waters 2489 type UV/Vis detector and an Empower 2 data processing system. Chromatographic conditions include:

chromatographic column: a Diamonsil C18 chromatographic column (4.6*250 mm, 5 μm); a mobile phase A is 50 mM ammonium formate (pH of formic acid is regulated to 3.0)-acetonitrile (90:10), and a mobile phase B is acetonitrile; gradient elute conditions: B is from 0% to 15% during 0-5 min, from 15% to 22% during 5-10 min, from 22% to 25% during 10-11 min, from 25% to 30% during 11-12 min and from 30% to 90% during 12-13 min, and B is 90% during 13-16 min; flow velocity: 1 ml·min$^{-1}$; column temperature: 30° C.; detection wavelength: 273 nm; and sample size: 20 μL. Retention time of a calcium dibutyryladenosine cyclophosphate main peak is about 11.5 min under the conditions. HPLC purity is detected according to the method in the following embodiments.

The anhydrouscalcium dibutyryladenosine cyclophosphate solids, DBC-Ca.2.3H$_2$O crystals (calcium dibutyryladenosine cyclophosphate 2.3 hydrates) in the following embodiments are purchased from Shanghai First Biological and Chemical Medication Co., Ltd.

Embodiment 1 Preparation of the Crystal-Water-Free Calcium Dibutyryladenosine Cyclophosphate Crystal Form Steps: weighing 10 g of the anhydrouscalcium dibutyryladenosine cyclophosphate solids, adding 40 ml of methanol, heating, stirring, dissolving, adding 0.3 g of activated carbon for decoloration, stirring for 15 min, filtering insoluble substances and obtaining filtrate; and slowly dripping 100 mL of ethyl ether into the filtrate, dripping for 2 h, maintaining room temperature, stirring and crystallizing for 8 h, separating out white solids, filtering and drying solids and obtaining the crystal-water-free calcium dibutyryladenosine cyclophosphate crystal form. The HPLC purity is 95.4%, and the yield is 88%.

Embodiment 2 Preparation of the Crystal-Water-Free Calcium Dibutyryladenosine Cyclophosphate Crystal Form Steps: weighing 10 g of the anhydrouscalcium dibutyryladenosine cyclophosphate solids, adding 40 ml of methanol, heating, stirring, dissolving, adding 0.5 g of activated carbon for decoloration, stirring for 15 min, filtering insoluble substances and obtaining filtrate; and slowly dripping 120 mL of methylbenzene into the filtrate, dripping for 2 h, maintaining a temperature of 5° C.-10° C., stirring and crystallizing for 5 h, separating out white solids, filtering and drying solids and obtaining the crystal-water-free calcium dibutyryladenosine cyclophosphate crystal. The HPLC purity is 95.2%, and the yield is 90%.

Embodiment 3 Preparation of the Crystal-Water-Free Calcium Dibutyryladenosine Cyclophosphate Crystal Form Steps: weighing 10 g of the anhydrouscalcium dibutyryladenosine cyclophosphate solids, adding 40 ml of methanol and 10 mL of acetone, heating, stirring, dissolving, adding 0.3 g of activated carbon for decoloration, stirring for 30 min, filtering insoluble substances and obtaining filtrate; and slowly dripping 130 mL of methyl tertiary butyl ether into the filtrate, dripping for 3 h, maintaining a temperature of 0-5° C., stirring and crystallizing for 5 h, separating out white solids, filtering and drying solids and obtaining the crystal-water-free calcium dibutyryladenosine cyclophosphate crystal. The HPLC purity is 96.2%, and the yield is 89%.

Embodiment 4 Preparation of the Crystal-Water-Free Calcium Dibutyryladenosine Cyclophosphate Crystal Form Steps: weighing 10 g of the anhydrouscalcium dibutyryladenosine cyclophosphate solids, adding 35 ml of ethanol, beating, stirring, dissolving, adding 0.5 g of activated carbon for decoloration, stirring for 15 min, filtering insoluble substances and obtaining filtrate: and slowly dripping 130 mL of methyl tertiary butyl ether into the filtrate, dripping for 3 h, maintaining a temperature of 0-5° C., stirring and crystallizing for 5 h, separating out white solids, filtering and drying solids and obtaining the crystal-water-free calcium dibutyryladenosine cyclophosphate crystal. The HPLC purity is 95.8%, and the yield is 93%.

Embodiment 5 Preparation of the Crystal-Water-Free Calcium Dibutyryladenosine Cyclophosphate Crystal Form Steps: weighing 10 g of the anhydrouscalcium dibutyryladenosine cyclophosphate solids, adding 35 ml of ethanol, heating, stirring, dissolving, adding 0.5 g of activated carbon for decoloration, stirring for 30 min, filtering insoluble substances and obtaining filtrate; and slowly dripping 120 mL of normal hexane into the filtrate, dripping for 3 h, maintaining a temperature of 0-5° C., stirring and crystallizing for 8 h, separating out white solids, filtering and drying solids and obtaining the crystal-water-free calcium dibutyryladenosine cyclophosphate crystal. The HPLC purity is 95.2%, and the yield is 90%.

Embodiment 6 Preparation of the Crystal-Water-Free Calcium Dibutyryladenosine Cyclophosphate Crystal Form Steps: weighing 10 g of the anhydrouscalcium dibutyryladenosine cyclophosphate solids, adding 60 ml of isopropanol, heating, stirring, dissolving, adding 0.5 g of activated carbon for decoloration, stirring for 15 min, filtering insoluble substances and obtaining filtrate; and slowly dripping 120 mL of normal hexane into the filtrate, dripping for 2 h, maintaining a temperature of 5° C.-10° C., stirring and crystallizing for 8 h, separating out white solids, filtering and drying solids and obtaining the crystal-water-free calcium dibutyryladenosine cyclophosphate crystal. The HPLC purity is 95.3%, and the yield is 89%.

Embodiment 7 X-Ray Powder Diffraction Detection of the Crystal-Water-Free Calcium Dibutyryladenosine Cyclophosphate Crystal Form The X-ray powder diffraction is performed by using the D8 ADVANCE X-ray powder diffractometer from the German company BRUKER-AXS, and test conditions include: the Cu target, the Kα light source (λ=1.54056 Å), the working voltage of 40 KV, the working current of 40 mA, the step length of 0.02, the scanning speed of 0.3 second per step, and the scanning angle of 1.5-60.0°. The X-ray powder diffraction patterns of the crystal-water-free calcium dibutyryladenosine cyclophosphate crystal form prepared in embodiments 1-6 are shown in FIG. 1, wherein parameters such as a diffraction angle of 2θ of each characteristic peak, interplanar spacing and relative intensities of characteristic peaks are shown in the following table:

| Diffraction peak No. | 2θ angle (°) | Interplanar spacing (Å) | Relative intensity (%) |
|---|---|---|---|
| 1 | 5.292 | 16.684 | 7 |
| 2 | 12.345 | 7.164 | 100 |
| 3 | 17.583 | 5.040 | 20 |
| 4 | 18.038 | 4.914 | 8 |
| 5 | 21.385 | 4.152 | 56 |
| 6 | 24.719 | 3.599 | 58 |
| 7 | 25.292 | 3.518 | 26 |
| 8 | 27.762 | 3.211 | 54 |
| 9 | 33.229 | 2.694 | 14 |
| 10 | 35.248 | 2.544 | 7 |
| 11 | 37.358 | 2.405 | 13 |
| 12 | 39.246 | 2.294 | 6 |
| 13 | 43.362 | 2.085 | 11 |
| 14 | 50.847 | 1.794 | 9 |

Figure 2:
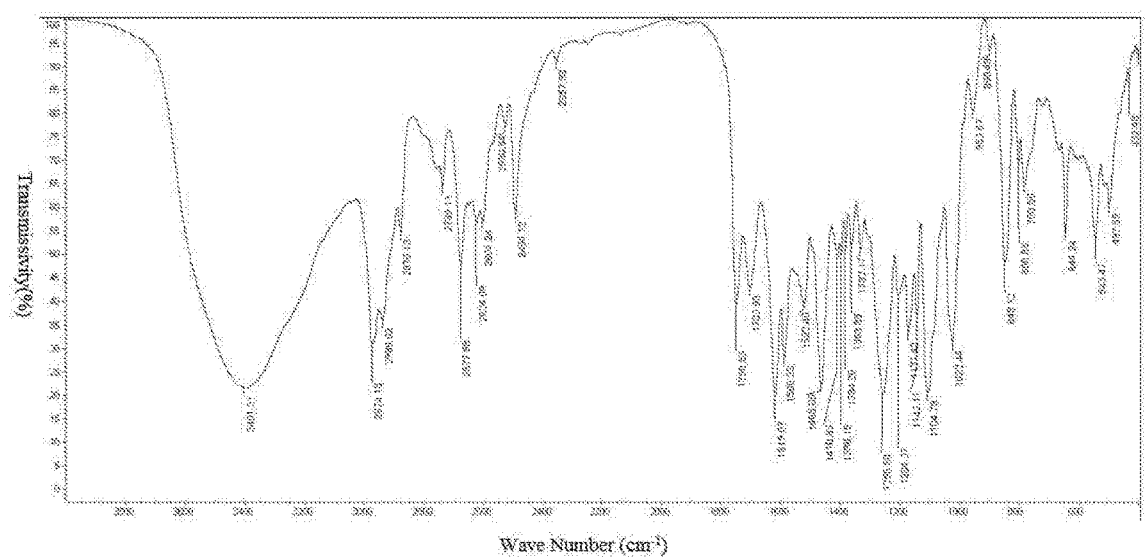
FIG. 2 is an Infrared Spectrogram (IR) of a crystal-water-free calcium dibutyryladenosine cyclophosphate crystal form prepared by the present invention.

Embodiment 8 Infrared Spectrum Detection of the Crystal-Water-Free Calcium Dibutyryladenosine Cyclophosphate Crystal Form An EQUINOX 55 infrared spectrometer from German Bruker is used, and a test method is as follows:

The crystal-water-free calcium dibutyryladenosine cyclophosphate crystal form provided by the present invention uses KBr pellets and the determined IR spectrum is scanned from 400 to 4000 $cm^{-1}$. As shown in FIG. 2, positions of characteristic peaks of the infrared spectrum include 2974, 1751, 1704, 1619, 1465, 1256, 1105 and 1022 $cm^{-1}$.

Figure 3:
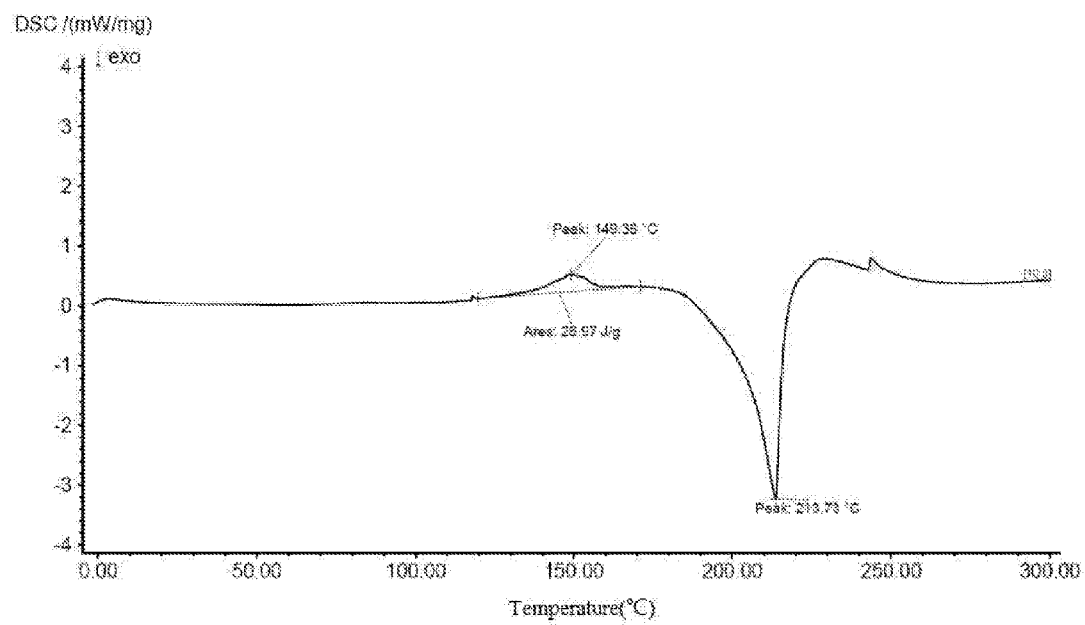
FIG. 3 is a Differential Scanning Calorimetry (DSC) map of a crystal-water-free calcium dibutyryladenosine cyclophosphate crystal form prepared by the present invention.

Embodiment 9 DSC Detection of the Crystal-Water-Free Calcium Dibutyryladenosine Cyclophosphate Crystal Form ADSC 204 F1 differential scanning calorimeter from German Netzsch is used, and operating conditions include:
a reference substance of a pan Al, an atmosphere of $N_2$, a temperature benchmark substance of metal indium, a temperature rise rate of 10K/min, and a temperature rise range of 0-300° C.
The result shows that the crystal-water-free calcium dibutyryladenosine cyclophosphate crystal form does not contain any crystal water.
The DSC diagram is shown in FIG. 3, has the maximum heat absorption peak value at a temperature of 120° C.-170° C., particularly has the maximum absorption peak at a temperature of 149.4° C., and has a melting enthalpy of about 26.971/g.

Figure 4:
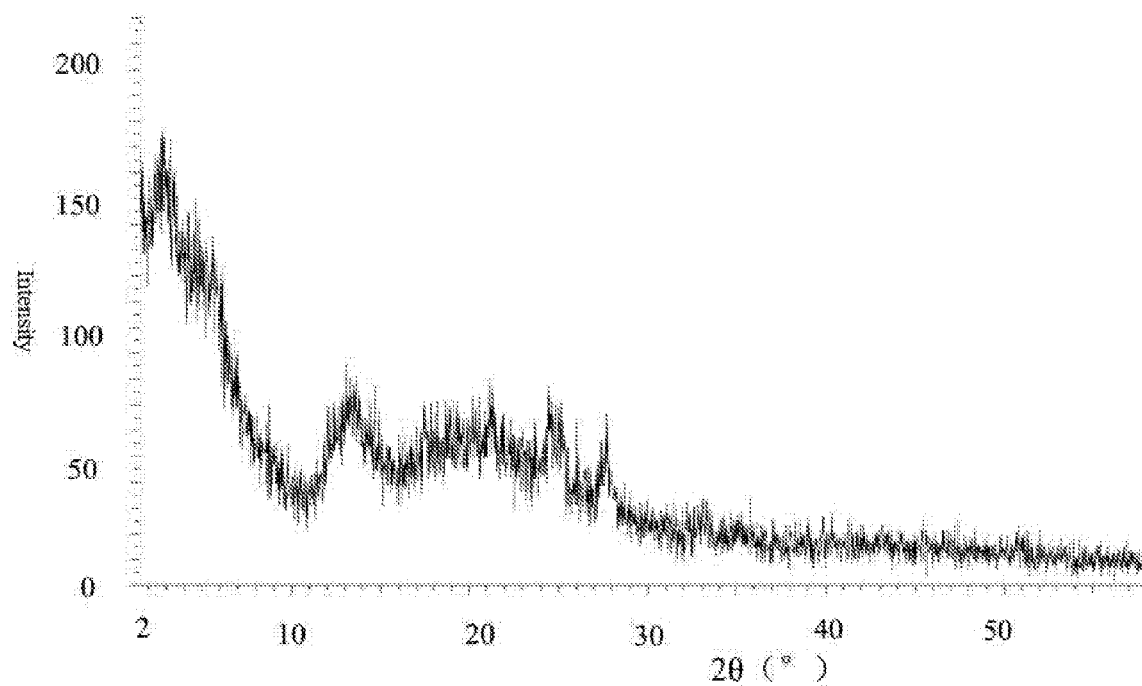
FIG. 4 is an X-ray Powder Diffraction Pattern (XRPD) of anhydrouscalcium dibutyryladenosine cyclophosphate solids.

Embodiment 10 X-Ray Powder Diffraction Detection of Anhydrouscalcium Dibutyryladenosine Cyclophosphate Solids Test conditions are the same as those in Embodiment 7, an X-ray powder diffraction pattern of the solids is shown in FIG. 4, and the result shows that the solids are amorphous substances.

Embodiment 11 Hydrogen Nuclear Magnetic Resonance ($^1$HNMR) of the Anhydrouscalcium Dibutyryladenosine Cyclophosphate Solids Avance III 400 MHz from the Bruker company is used in hydrogen nuclear magnetic resonance detection, and a test method includes steps: adding 5 mg of anhydrous calcium dibutyryladenosine cyclophosphate solid crude drugs into a nuclear magnetic resonance tube, dissolving with deuterium oxide, scanning to obtain the hydrogen nuclear magnetic resonance; and the result data are: $^1$HNMR (400 MHz, D2O): delta is equal to 8.58 (s, 1H); 8.37 (s, 1H); 6.29 (s, 1H); 5.64-5.61 (d, 1H); 5.12-5.06 (m, 1H); 4.46-4.37 (m, 1H); 4.28-4.20 (m, 2H); 2.51-2.40 (m, 4H); 1.69-1.53 (m, 4H); 0.93-0.88 (t, 3H); 0.87-0.83 (t, 3H).

Embodiment 12 Mass Spectrum (MS) of the Anhydrouscalcium Dibutyryladenosine Cyclophosphate Solids An ACQUITY™ UPLC&Q-TOF MS Premier from the American Waters is used in mass spectrometric detection, and a test method is as follows:
the chromatographic column is a Waters Acquity BEH C18 chromatographic column (2.1×100 mm, 1.7 μm), a tandem mass spectrometryionization source refers to an electrospray ionization source (ESI), detection is performed in a positive ion scanning manner, a capillary voltage is 3.0 kV, a temperature of the ionization source is 100° C., a temperature of atomization gas is 350° C., flow of the atomization gas is 600.0 L-hr-1, collision voltages are respectively 4.0 eV (MS) and 15.0-30.0 eV (MS/MS), and a scanning range is m/z 100-1000. A detected molecular ion peak m/z is 469.4.

Embodiment 13 Acceleration Test and Room-Temperature Long-Term Observation Study on Stability 1. an acceleration test includes steps: adding totally five batches of samples such as the crystal-water-free calcium dibutyryladenosine cyclophosphate crystal form and the anhydrous calcium dibutyryladenosine cyclophosphate solids prepared in Embodiment 1, and DBC-Ca.2.3H$_2$O crystals (calcium dibutyryladenosine cyclophosphate 2.3hydrates) into a constant temperature and humidity incubator with a relative humidity of 75±5% at a temperature of 30° C. according to the crude drug package, standing by 6 months, respectively sampling and detecting related substances (detected by the HPLC detection method) in the first month, the second month, the third month and the sixth month of the test, measuring the content, and comparing with results in 0 month, wherein the results are shown in Table 1.

TABLE 1

Hygrothermalacceleration test results of the crystal-water-free calcium dibutyryladenosine cyclophosphate crystal form andanhydrous solid powder

| | | Time | | | | |
|---|---|---|---|---|---|---|
| | Batch No. | 0 months | 1 month | 2 months | 3 months | 6 months |
| Crystal-water-free calcium dibutyryladenosine cyclophosphate crystal form | | | | | | |
| Related substances (%) | 110110 | 3.8% | 3.9% | 4.0% | 4.2% | 4.5% |
| | 110118 | 4.1% | 4.0% | 4.1% | 4.2% | 4.7% |
| | 110122 | 4.0% | 4.1% | 4.1% | 4.3% | 4.6% |
| Content (%) | 110110 | 95.8% | 95.3% | 95.1% | 94.9% | 94.5% |
| | 110118 | 96.2% | 95.8% | 95.4% | 95.0% | 94.7% |
| | 110122 | 95.2% | 95.0% | 95.1% | 94.7% | 94.3% |
| Anhydrouscalcium dibutyryladenosine cyclophosphate solids | | | | | | |
| Related substances (%) | 1101061 | 4.3% | 4.9% | 5.5% | 6.0% | 6.7% |
| Content (%) | 1101061 | 95.4% | 94.8% | 94.2% | 93.5% | 93.0% |
| DBC-Ca•2.3H$_2$O crystals | | | | | | |
| Related substances (%) | c1102171 | 5.3% | 5.5% | 5.8% | 5.9% | 6.1% |
| Content (%) | c1102171 | 90.2% | 90.1% | 89.8% | 89.7% | 89.3% |

2. long-term observation stability test includes steps: adding totally five batches of samples such as the crystal-water-free calcium dibutyryladenosine cyclophosphate crystal form and the anhydrous calcium dibutyryladenosine cyclophosphate solids prepared in Embodiment 1, and the DBC-Ca.2.3H$_2$O crystals (calcium dibutyryladenosine cyclophosphate 2.3 hydrates) into a constant temperature and humidity incubator with a relative humidity of 60±5% at a temperature of 16° C. according to the crude drug package (drugs are packaged by low-density polyethylene bags), standing by 12 months, respectively sampling and detecting the related substances (detected by the HPLC detection method) in the third month, the sixth month, the ninth month and the twelfth month of the test, measuring the content, and comparing with results in 0 month, wherein the results are shown in Table 2.

TABLE 2

Long-term stability test results of the crystal-water-free calcium dibutyryladenosine cyclophosphate crystal form andanhydrous solid powder

| | | Time | | | | |
|---|---|---|---|---|---|---|
| | Batch No. | 0 months | 3 months | 6 months | 9 months | 12 months |
| Crystal-water-free calcium dibutyryladenosine cyclophosphate crystal form | | | | | | |
| Related substances (%) | 110110 | 3.8% | 3.7% | 3.8% | 3.7% | 4.0% |
| | 110118 | 4.1% | 4.2% | 4.1% | 4.0% | 4.3% |
| | 110122 | 4.0% | 4.1% | 4.3% | 4.2% | 4.4% |
| Content (%) | 110110 | 95.8% | 95.5% | 95.6% | 95.5% | 95.3% |
| | 110118 | 96.2% | 96.1% | 96.0% | 95.9% | 95.8% |
| | 110122 | 95.2% | 95.3% | 95.1% | 95.0% | 94.9% |
| Anhydrouscalcium dibutyryladenosine cyclophosphate solids | | | | | | |
| Related substances (%) | 1101061 | 4.3% | 4.6% | 4.8% | 5.2% | 5.4% |
| Content (%) | 1101061 | 954% | 95.0% | 94.7% | 94.4% | 94.1% |
| DBC-Ca•2.3H$_2$O crystals | | | | | | |
| Related substances (%) | c1102171 | 5.3% | 5.3% | 5.5% | 5.6% | 5.9% |
| Content (%) | c1102171 | 90.2% | 90.0% | 89.9% | 89.7% | 89.6% |

Although specific embodiments of the present invention are described above, those skilled in the art shall understand that these embodiments are illustrations only, and may make multiple changes or modifications on these embodiments on the premise of not departing from the principle and essence of the present invention. Therefore, a scope of protection of the present invention is limited by attached claims.

What is claimed is:

1. A method for preparing a crystal-water-free calcium dibutyryladenosine cyclophosphate crystal form, comprising:

mixing anhydrous amorphous calcium dibutyryladenosine cyclophosphate solids with a solvent, dissolving the resulting mixture in the solvent at 25-60° C., and decolorizing by activated carbon;

filtering the mixture to remove insoluble substances, dropwise adding an anti-solvent into a filtrate, cooling the filtrate at 0-10° C. under stirring for 1-24 h and crystallizing to produce the crystal-water-free calcium dibutyryladenosine cyclophosphate crystal form;

wherein the crystal-water-free calcium dibutyryladenosine cyclophosphate crystal form has characteristic peaks at diffraction angles 2θ of 12.3°±0.2°, 17.60°±0.2, 21.4°±0.2°, 24.7°±0.2, 25.3°±0.2° and 27.8°±0.2° in an X-ray powder diffraction pattern taking Cu-Kα as a radiation source; and the differential scanning calorimetry map is as shown in FIG. 3.

2. The method of claim 1, wherein the solvent is selected from the group consisting of methanol, ethanol, isopropanol, ethylene glycol, acetonitrile, tetrahydrofuran, dioxane, ethyl acetate, dichloromethane, acetone and chloroform; the anti-solvent is selected from the group consisting of normal hexane, n-pentane, ethyl ether, isopropyl ether, methyl tertiary butyl ether and methylbenzene.

3. The method of claim 1, wherein a volume-to-weight ratio of the solvent to the anhydrous calcium dibutyryladenosine cyclophosphate solids is 2-10 mL/g; and/or a weight ratio of the activated carbon to the anhydrous calcium dibutyryladenosine cyclophosphate solids is (0.01-0.1):1.

4. The method claim 3, wherein an adding rate of the anti-solvent is 0.3-2.0 mL/min.

* * * * *